(12) United States Patent
Parry et al.

(10) Patent No.: US 8,728,165 B2
(45) Date of Patent: May 20, 2014

(54) ORTHOPAEDIC IMPLANTS AND PROTHESES

(75) Inventors: John Parry, Worcestershire (GB); Jeffrey Johnson, Worcestershire (GB)

(73) Assignee: Centinel Spine, Inc., New York, NY (US)

( * ) Notice: Subject to any disclaimer, the term of this patent is extended or adjusted under 35 U.S.C. 154(b) by 976 days.

(21) Appl. No.: 11/938,476

(22) Filed: Nov. 12, 2007

(65) Prior Publication Data

US 2008/0183293 A1 Jul. 31, 2008

(51) Int. Cl.
*A61F 2/44* (2006.01)
(52) U.S. Cl.
USPC ............. 623/17.16; 623/17.11; 606/246
(58) Field of Classification Search
USPC .......... 623/17.16, 17.11; 606/246, 86 A, 279, 606/61
See application file for complete search history.

(56) References Cited

U.S. PATENT DOCUMENTS

| 5,531,746 | A * | 7/1996 | Errico et al. | 606/287 |
|---|---|---|---|---|
| 2002/0004683 | A1* | 1/2002 | Michelson | 623/17.16 |
| 2002/0055741 | A1* | 5/2002 | Schlapfer et al. | 606/71 |
| 2002/0099376 | A1* | 7/2002 | Michelson | 606/61 |
| 2003/0078668 | A1* | 4/2003 | Michelson | 623/17.16 |
| 2003/0125739 | A1* | 7/2003 | Bagga et al. | 606/61 |
| 2004/0024464 | A1* | 2/2004 | Errico et al. | 623/17.16 |
| 2005/0004683 | A1* | 1/2005 | Yamazaki | 700/30 |
| 2005/0187552 | A1* | 8/2005 | Michelson | 606/69 |
| 2006/0085071 | A1* | 4/2006 | Lechmann et al. | 623/17.11 |
| 2006/0247771 | A1* | 11/2006 | Peterman et al. | 623/17.11 |
| 2007/0276498 | A1* | 11/2007 | Aebi et al. | 623/17.16 |
| 2007/0293948 | A1* | 12/2007 | Bagga et al. | 623/17.11 |
| 2008/0249575 | A1* | 10/2008 | Waugh et al. | 606/305 |
| 2010/0305704 | A1* | 12/2010 | Messerli et al. | 623/17.16 |

FOREIGN PATENT DOCUMENTS

WO 02058593 8/2002

OTHER PUBLICATIONS

Examination Report for corresponding Great Britain Appl. No. 0721478.6 dated Mar. 29, 2012.

* cited by examiner

*Primary Examiner* — Sameh Boles
*Assistant Examiner* — Samuel Hanna
(74) *Attorney, Agent, or Firm* — Monument IP Law Group

(57) ABSTRACT

The present invention provides cervical implant (30) comprising an upper surface (38), a lower surface (40), a posterior portion (34) and an anterior portion (36) and including a perimeter (42) and one or more apertures (44,46) within said anterior portion for receiving securing means, said apertures having respective longitudinal axes M1, M2, characterized in that said axes extend in a direction substantially through said anterior portion (36) and converge at a point in a plane outside of said perimeter (42).

8 Claims, 4 Drawing Sheets

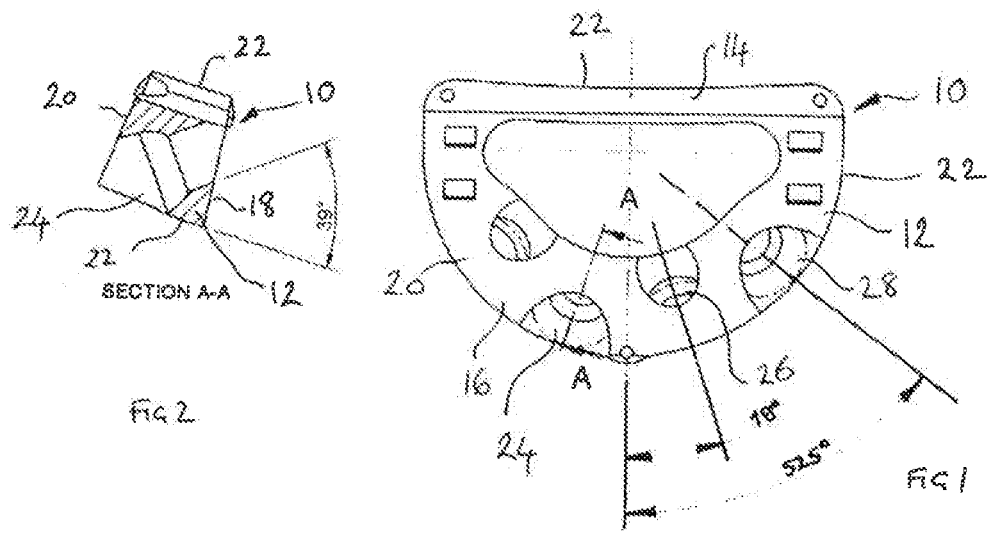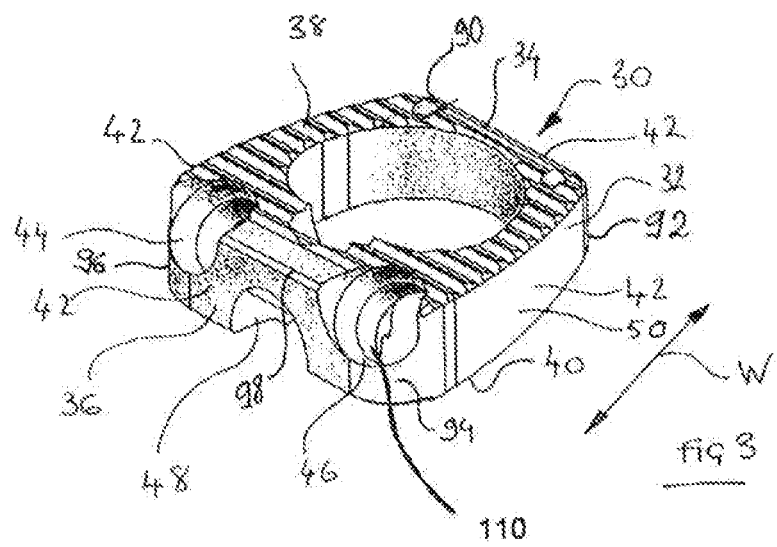

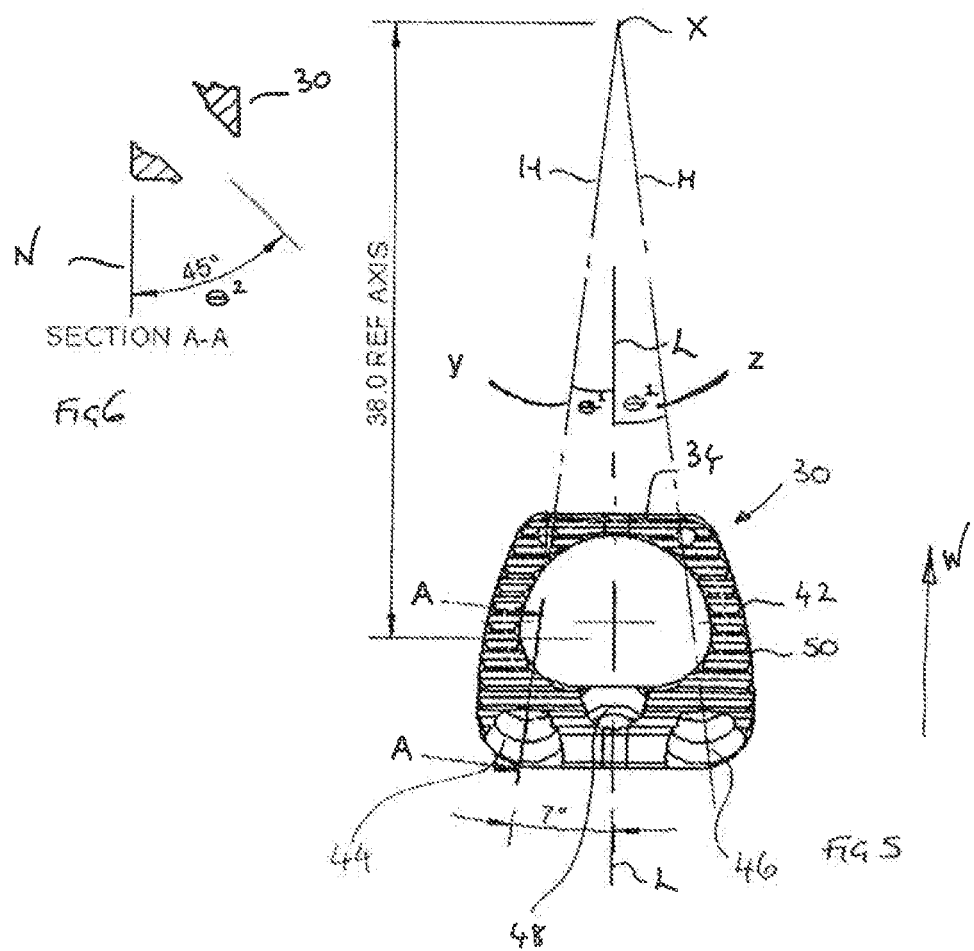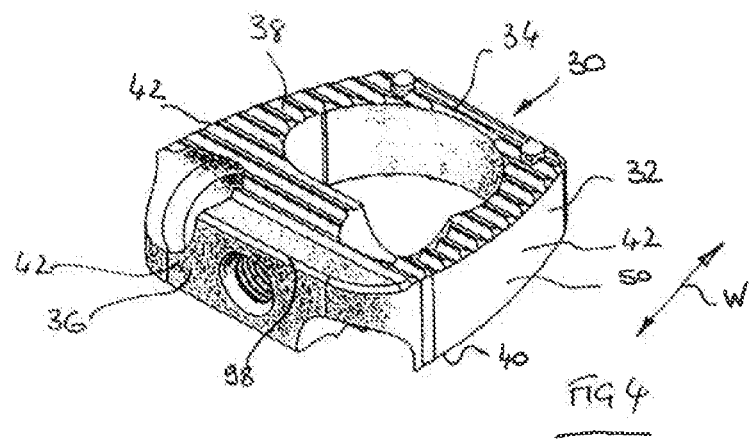

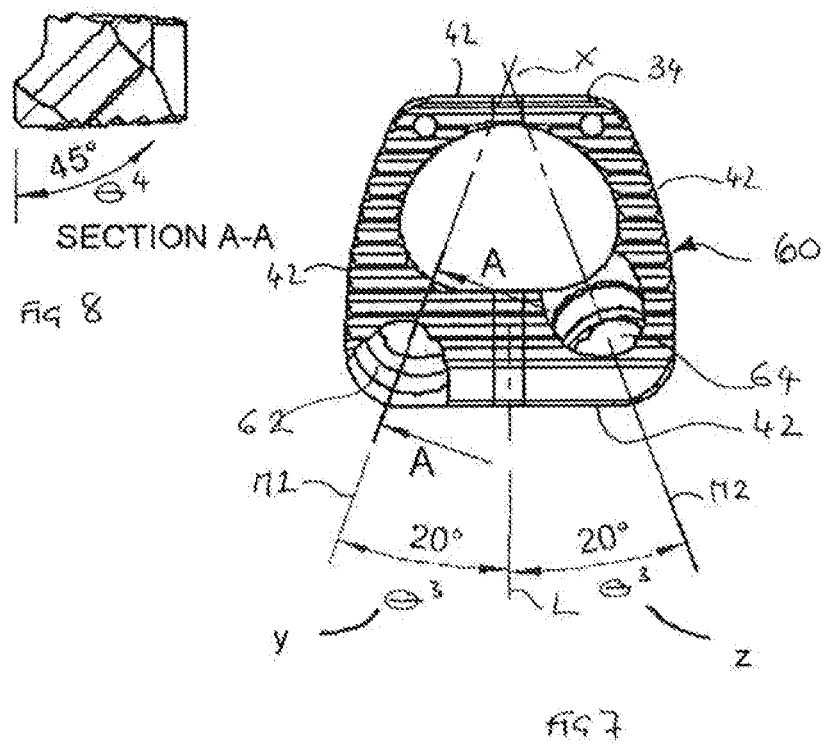

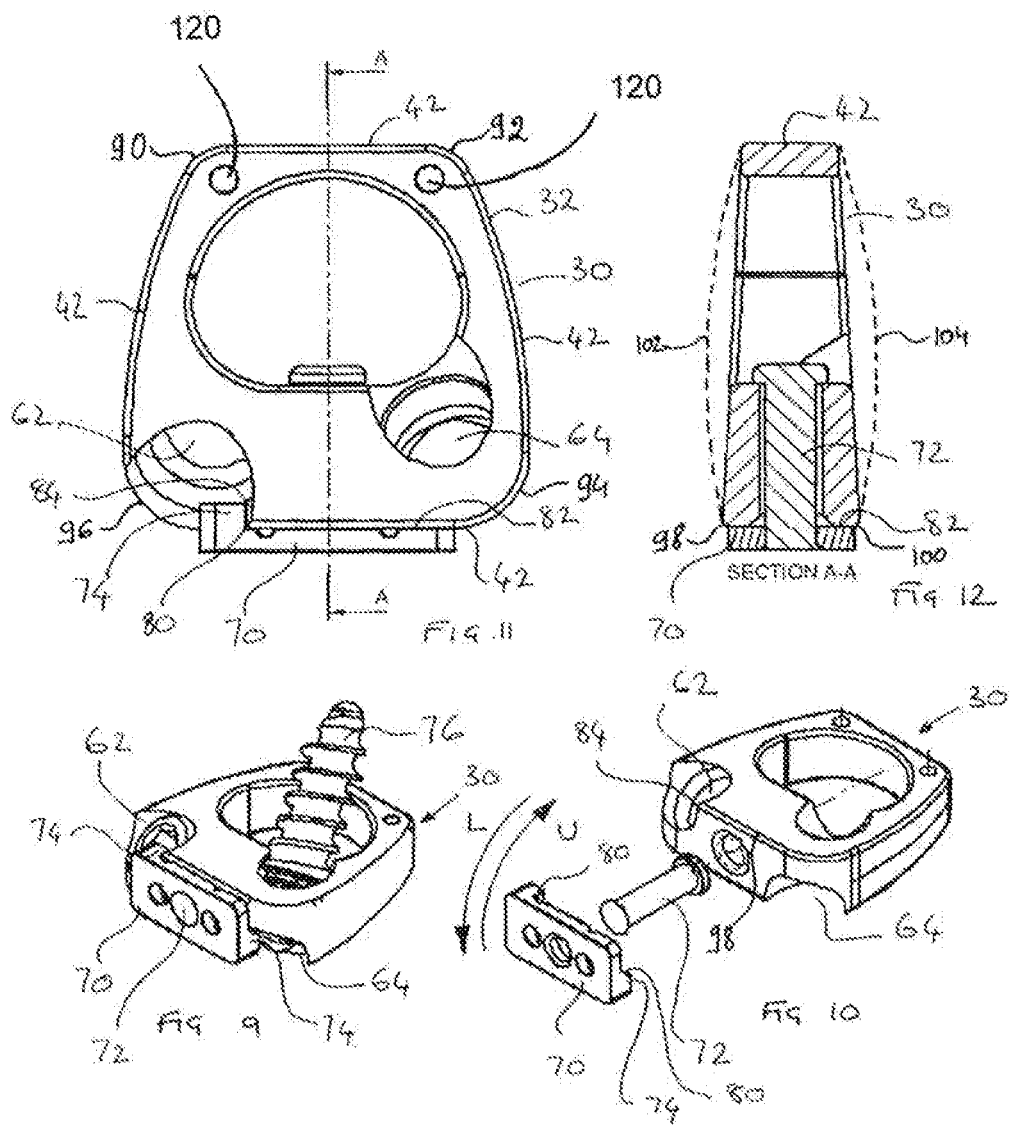

ORTHOPAEDIC IMPLANTS AND PROTHESES

The present invention relates to orthopaedic implants and prostheses and relates particularly but not exclusively to implants and prostheses for bone structures, particularly in the cervical region.

BACKGROUND ART

Bones and related structural body parts, for example spine and/or vertebral bodies and/or inter-vertebral discs, may become crushed or damaged as a result of trauma/injury, or damaged by disease (e.g. by tumour, auto-immune disease), or damaged as a result of degeneration through an aging process. In many such cases the structure can be repaired by replacing the damaged parts (e.g. vertebra and/or discs) with a prosthesis or implant. A method of repair is to remove the damaged part(s) (e.g. vertebra and/or partial vertebra and/or disc and/or partial disc) and replace it with an implant or prosthesis such that the implant or prosthesis is free standing or fastened in position between adjacent undamaged parts (e.g. adjacent vertebral bodies).

Associated with this method of repair, is fusion of the bone structure where the implant or prosthesis is placed. Typically an implant or prosthesis may consist of a central space surrounded by a continuous wall that is open at each end (e.g. superior and inferior). This form of implant or prosthesis is thought to allow bone to develop within the central space, developing from each extremity of the implant or prosthesis towards the centre. Typically an implant or prosthesis is secured directly to a bone structure by mechanical or biological means.

Many current implants and prostheses are hollow to allow bone growth within the hollow space. One problem, when replacing large structural sections, is that the relationship of length (or height) to cross sectional area of the central space is large. The larger this relationship, the more problems arise in providing an adequate blood and nutrient supply to allow fusion and or bone growth into the hollow centre, either in a timely manner, or at all. One solution to this problem is to make the central space with as large a cross section as possible. However, this is limited by the wall thickness and the material used for the implant or prosthesis, which determines its mechanical strength. For this reason, orthopaedic surgeons often pack the space within the implant or prosthesis with an injectable or mouldable bone growth encouraging material or with fragments of bone taken from other parts of the patients body i.e. autograft or bone from biocompatible sources, for example allograft or synthetic bone. Even then there may not be complete fusion of the implant or prosthesis into the bone structure.

The implant or prosthesis is attached to the adjacent vertebral body using a fixing e.g. a screw. A problem generally with such fixing or fixing systems is that, after insertion into the vertebral body, the fixing can work itself loose and/or back-out i.e. withdraw from the vertebral body. The consequence of back-out or loosening of the implant or prosthesis includes loss of stability, potential risk to the patient and a separate costly and often painful operation.

One of the applicant's own well known product is protected under U.S. Pat. No. 4,904,261 and provides a generally horse shoe shaped implant for use between vertebrae in the lower spine area. The arrangement includes a plurality of screws extending therethrough and into the adjacent vertebra so as to ensure the implant is securely located once positioned by a surgeon. The screw arrangement in this design is such as to cause the screws to converge at a point within the boundary of the implant when viewed form above.

Cervical implants are particularly problematic to design as their positioning dictates a very small size and requires good security of location once implanted and a low profile so as to reduce any portions thereof that may otherwise extend beyond the boundary of the implant. The small dimensions of such implants make achieving these goals somewhat difficult and the market demand does not appear to have been adequately met.

It is an object of the present invention to provide an improved cervical implant that may address one or more of the above-mentioned issues.

Accordingly, the present invention provides a cervical implant comprising an upper surface, a lower surface, an anterior portion and a posterior portion and including a perimeter and one or more apertures within said anterior portion for receiving securing means, said apertures having respective longitudinal axes $M1$, $M2$, wherein said axes extend in a direction substantially through said anterior portion and converge at a point in a plane outside of said perimeter.

Advantageously, one or more of said apertures include guide portions for engagement with corresponding guide portions on corresponding securing means and wherein said guide portions maintain said securing means substantially within a 3 degree cone angle. Preferably, the centre lines of the apertures as shown on the plan view the (ref axes $M1$, $M2$) converge at an angle of between 13 and 15 degrees.

The implant includes a horizontal plane and said axes $M1$, $M2$ extend at an angle of between Y and Z (each angle Y and Z falling within the range of about 20 degrees) from said horizontal plane and may be provided with an interior portion for receiving bone growth material and said axes $M1$, $M2$ may extend through said interior portion.

Preferably, the implant includes a retaining means for retaining one or more securing means within said implant. Said retaining means may include a plate portion securable to said implant and covering one or more of said apertures when secured, thereby to prevent removal of one or more securing means.

In one arrangement the retaining means comprises a rotatable plate portion secured to said implant at a rotation mount and wherein said plate portion is rotatable between a first position in which it acts to obturate one or more apertures and a second position in which it acts to unbturate one or more of said apertures.

Preferably, the plate portion includes one or more projections for engagement with one or more of said securing means and includes apertures for fixation devices which connect to vertebrae.

Advantageously, the implant includes a frictional engagement portion for frictionally engaging the implant and the plate such as to resist rotation of the plate once in its obturation mode.

Preferably, the implant includes one upwardly projecting aperture and one downwardly projecting aperture. Alternatively, the implant includes two apertures extending generally in a first direction and one aperture extending in a second direction.

Preferably, the implant includes one or more securing means, such as a screw or the like and one or more of said one or more securing means includes an anti-back out feature.

In one arrangement one or more of said surfaces comprises a domed surface but in an alternative arrangement, said surfaces extend in convergent planes.

The implant may include one or more location markers and may be provided as a kit comprising a selection of different height implants.

Although the following discussion focuses on spinal implants or prostheses, it will be appreciated that many of the principles may equally be applied to other bone structures within the human or animal body.

The present invention will now be more particularly described by way of example with reference to the accompanying drawings in which:

FIGS. 1 and 2 are respective plan and side elevations of a prior art arrangement;

FIG. 3 is a general view of a first arrangement of the present invention;

FIG. 4 is a general view of a second arrangement of the present invention;

FIGS. 5 and 6 are respective plan and cross-sectional views of the arrangement of FIG. 3;

FIGS. 7 and 8 are respective plan and cross-sectional views of the arrangement of FIG. 4; and FIGS. 9 to 12 illustrate a further modification of a locking mechanism that may be employed to secure any screws within the implant and prevent what is commonly referred to as "back-out".

Referring to FIG. 1 which illustrates the prior art, a spinal implant or prosthesis 10 comprises a cage portion 12 for insertion between vertebrae and including posterior and anterior portions 14, 16 and upper and lower surfaces 18, profiled to correspond with the profile of any bone material to which they are to be secured. An outer perimeter 22 is defined by the surface extending between the upper and lower surfaces 18, 20 and when viewed from above defines a generally "horseshoe" shape. One or more holes 24, 26, 28 are provided through which securing means (not shown) may be inserted so as to secure the device to respective superior and inferior vertebral bodies (not shown). The securing means may be screws, pins, staples, bollards or any other suitable fastening device.

FIG. 2 is a cross-sectional view taken through one of the holes in FIG. 1 and illustrates the angle of attack for any screw placed therein. In practice, the angle is substantially 39 degrees and each hole is circumferentially displaced relative to its neighbour such that any screws placed therein and emerging therefrom converge at a point within the boundary of the cage, when viewed from above.

The arrangement of the present invention is shown in FIGS. 3 to 8 and the implant itself comprises a spinal implant or prosthesis 30 suitable for use in the cervical region of the spine and which includes a cage portion 32 for insertion between vertebrae and further includes a posterior and anterior portions 34, 36 and upper and lower surfaces 38, 40 profiled to correspond with the profile of any bone material to which they are to be secured. An outer perimeter 42 is defined by the surface extending between the upper and lower surfaces 38, 40 and when viewed from above defines a generally wedge shaped structure. One or more holes 44, 46, 48 are provided through which securing means (not shown) may be inserted so as to secure the device to respective superior and inferior vertebral bodies (not shown). The securing means may be screws, pins, staples, bollards or any other suitable fastening device. Advantageously, one or more of said apertures include guide portions 110 for engagement with corresponding guide portions on corresponding securing means (not shown) and wherein said guide portions 110 maintain said securing means substantially within a 3 degree cone angle. FIG. 4 illustrates a two hole arrangement discussed in more detail later herein. The implant may include one or more location markers 120 and may be provided as a kit comprising a selection of implants of differing heights.

In contrast with the arrangement of FIGS. 1 and 2, the arrangement of FIGS. 3 and 4 is generally much flatter and less circular in form and includes a sidewall portion 50 which extends in the direction of arrow W. The reader will also appreciate the aperture arrangement of this implant differs from the above in that a upwardly extending hole 48 is provided along with one or more generally downwardly extending holes 44, 46 and those holes extend in a direction and at an angle which results in them converging at a point X in a plane outside of the perimeter 42 thereof. The plan view of FIG. 5 aptly illustrates the angular relationship between the two holes 44, 46 and from which the reader will appreciate that the holes are angled at an angle $\theta 1$ of 7 degrees from a longitudinal axis L and the hole axes H cross each other outside of the perimeter 42 and below the implant itself. The vertical angular relationship is shown in FIG. 6 which illustrates the hole axes H extend at an angle $\theta 2$ of approximately 45 degrees when measured from the neutral horizontal plane N. The angles $\theta 1$ and $\theta 2$ may be varied from the above so long as the arrangement still converges outside of the perimeter and as long as the vertical angle $\theta 2$ is such as to maintain any screw within the vertebral body into which it is inserted. In practice, it has been found that for relatively small cervical cages it is desirable to maintain angle $\theta 1$ at between 5 and 10 degrees and preferably between 6 and 8 degrees and maintain angle $\theta 2$ at between 40 and 50 degrees and preferably between 44 and 46 degrees. The central hole 48 in FIG. 5 extends upwardly at the angle shown in FIG. 6 and as modified above and in practice any screw positioned therein will pass between downwardly extending screws of an implant positioned between lower vertebral bodies. Thus, it will be appreciated that the angular positioning of the holes is important to the effective operation of the implant and the ability to "stack" implants in adjacent multilevel procedures without the securing means interfering with each other. This is a particular problem in the cervical region as space is at a premium and the security of any implant is of particular concern.

FIGS. 7 and 8 illustrate another arrangement 60 the present invention in which only two holes 52, 54 are provided for receiving appropriate screws or the like (not shown). These holes have centre lines or axes M1 and M2 which are angled relative to longitudinal axis L by an angle $\theta 3$ of 20 degrees and, again, the arrangement is such as to cause the hole centre lines or axes M1 and M2 to cross at a point X in a plane outside of the perimeter 42 of the implant itself. The vertical angular relationship is shown in FIG. 7 and is the same for both holes which extend at an angle $\theta 4$ of 45 degrees from the horizontal and vertical planes. It will be appreciated that the angles $\theta 3$ and $\theta 4$ may be varied slightly so long as the same basic principle of the axes crossing outside of the boundary is observed. For example $\theta 3$ could be between 18 and 22 degrees depending on the depth of the implant and angle $\theta 4$ could be varied as discussed above.

FIGS. 9 to 12 illustrate a further feature of the present invention which helps secure any screws in the implant once they have been screwed into the surrounding vertebral body. From FIG. 9 it will be appreciated that the locking mechanism includes a rotatable blocking plate 70 which rotates about mounting pin 72 secured to the implant itself. In one position of the mechanism it acts to unobturate the holes whilst in a second position it acts to obturate them and prevent any screw inserted therein from reversing out of the implant or suffering from "back-out". FIGS. 9 and 11 shows the plate 70 in the obturating mode but it will be appreciated that the unobturated mode is achieved by simply turning the plate in the direction of arrow U such that it extends substantially vertically rather than substantially horizontally. An additional feature of the locking mechanism is one or more projections 74 which extend from the plate 70 and towards any screw 76 that might be inserted within an associated hole. These projections assist with the securing of the screws by virtue of the fact that they reduce the distance that any screw can back-out before they engage with the plate. Indeed, these projections could be sized such as to positively engage with the head of any screw.

A still further possible feature of this plate arrangement is a frictional engagement portion 78 comprising a minor detent 80 on an inner surface 82 of the plate which, in operation, is sized such that it engages on an edge 84 of an associated hole when the plate 70 is in its obturating position and is caused to ride over said edge when the plate is moved but the force required to complete such a displacement is greater than the plate would experience in normal use of the insert but less than can be generated by a surgeon whilst installing or removing the insert, particularly if a tool of some type is employed. Such a feature may be provided in association with one or other or both holes.

Common to all the arrangements shown herein and discussed above is the additional but optional feature of curved surfaces 90, 92 or edges on the posterior portion and 94, 96 on the anterior portion. Such curved surfaces help reduce frictional interference with adjacent body portions. Additional to this feature is the provision of curved edges 98, 100 around the upper and lower surfaces 38, 40 as they adjoin the perimeter 42. One or other or both of the upper and lower surfaces 38, 40 may be domed as shown by dotted lines 102 and 104 of FIG. 12, thereby to more accurately conform to some patient vertebrae profiles.

It will be appreciated that the implant may be formed of a radio-translucent material, such as polyether-etherketone (PEEK), which means that the cage will not obscure inspection of the degree of bone growth inside the cage when imaged by x-rays. Additionally, the may be formed of a bio-resorbable material. The bio-resorbable material is preferably osteo-conductive or osteo-inductive (or both). The implant may be formed of a bio-resorbable material. The bio-resorbable material is preferably osteo-conductive or osteo-inductive (or both).

Some practitioners prefer to allow some degree of movement between the implant and the adjacent vertebral body after implantation. In that case the screws would not be fully tightened. Others prefer a more rigid implant, which is firmly locked to the adjacent vertebral body. This implant allows either preference.

The implant described above is a unitary device that is inserted in one plane and is self centering, is conformable to surrounding anatomy, matches anatomical geometry, and matches natural anterior anatomical load constraints.

It will be appreciated that, instead of having one superior hole and two inferior holes in the implant as shown in the drawings, the implant may have two superior and one inferior holes, or may be adapted to have two superior holes and one inferior holes.

It will also be appreciated that the angular positioning of the various holes, as described above, allows the present insert to be of a relatively small size and therefore insertable within the inter vertebral space in the cervical region, where space is at a premium, whilst still allowing for the securing of said implant by conventional means. Thus, it will be appreciated that the angular positioning of the holes is important to the effective operation of the implant and the ability to "stack" implants in adjacent multilevel procedures without the securing means interfering with each other, which can be of major significance in some situations.

The locking plate provides a means for ensuring the security and location of the implant once inserted but may be reversed so as to allow removal of the securing screws if a revision is required.

The invention claimed is:

1. A cervical implant for stabilizing adjacent vertebral bodies in the cervical area, the cervical implant comprising:
   one or more securing means;
   an upper surface having a contact area configured for engaging a superior vertebrae of the adjacent vertebral bodies, a lower surface having a contact area configured for engaging an inferior vertebrae of the adjacent vertebral bodies, an outer perimeter surface extending in between said upper and lower surfaces, said outer perimeter surface including an anterior side surface, and an posterior side surface, the anterior and posterior side surfaces having superior and inferior curved edges that adjoin said outer perimeter surface to the upper and lower surfaces of the implant, respectively, and being configured to reduce frictional interference with adjacent body portions, the implant further comprising one upwardly projecting through aperture that extends through said anterior side surface and the upper surface of the implant, and one downwardly projecting through aperture that extends through said anterior side surface and the lower surface of the implant for receiving said one or more securing means, each of said through apertures having proximal and distal openings and a channel extending therebetween, said apertures having respective longitudinal axes M1, M2 that extend along and through said channels of said apertures, and said proximal openings of said apertures lying within angled planes relative to said outer perimeter surface, such that a first angled plane extends across said lower surface and said outer perimeter surface, and a second angled plane extends across said lower surface and said outer perimeter surface; said axes extending in an angled direction through said anterior side surface of said outer perimeter surface and converging at a point in a plane outside of said posterior side surface of said outer perimeter surface, wherein one or more of said through apertures include guide portions for engagement with corresponding guide portions on corresponding securing means, such that said guide portions maintain said securing means substantially within a 3 degree cone angle; and
   a retaining means for retaining said one or more securing means within said apertures, the retaining means comprising a rotatable plate securable to said anterior side surface of said implant by a rotation mount for covering said apertures of said implant at the same time when secured to prevent removal of said one or more securing means from said apertures, the plate being rotatable about said rotation mount between a first position in which said plate acts to obturate said apertures at the same time, and in a second position in which said plate acts to unobturate said apertures at the same time, said retaining means including one or more projections extending from an inner surface of said plate and configured for placement into said apertures when said plate is secured to the anterior side surface of said implant to positively engage a portion of said securing means when residing within the apertures to prevent said securing means from backing out, the retaining means further including a frictional engagement portion comprising a detent on said inner surface of the plate for engaging an edge of at least one of the apertures when deployed to resist further rotation of the plate in the obturated position relative to the implant.

2. The cervical implant as claimed in claim 1 wherein said axes M1 and M2 extending through the channels of said apertures converge at an angle of between 13 and 15 degrees.

3. The cervical implant as claimed in claim 1 further including a through opening extending through the upper and the lower surface for receiving bone growth material and wherein said axes M1, M2 extend through said through opening.

4. The cervical implant as claimed in claim 1 wherein one or more of said one or more securing means includes an anti-back out feature.

5. The cervical implant as claimed in claim 1 wherein one or more of said surfaces comprise a domed surface.

6. The cervical implant implant as claimed in claim 1 wherein said surfaces extend in convergent planes.

7. The cervical implant as claimed in claim 1 wherein said implant includes one or more location markers.

8. The cervical implant as claimed in claim 1, wherein the one or more securing means comprises a screw.

* * * * *